US011180725B2

(12) United States Patent
Johnson

(10) Patent No.: US 11,180,725 B2
(45) Date of Patent: Nov. 23, 2021

(54) SYSTEM AND METHOD FOR TRANSPORTING ALGAE

(71) Applicant: SIFTEX EQUIPMENT COMPANY, INC., South Windsor, CT (US)

(72) Inventor: Martin L. Johnson, Chester, VA (US)

(73) Assignee: SIFTEX EQUIPMENT COMPANY, INC., South Windsor, CT (US)

( * ) Notice: Subject to any disclaimer, the term of this patent is extended or adjusted under 35 U.S.C. 154(b) by 169 days.

(21) Appl. No.: 16/502,161

(22) Filed: Jul. 3, 2019

(65) Prior Publication Data

US 2020/0010790 A1 Jan. 9, 2020

Related U.S. Application Data

(60) Provisional application No. 62/695,262, filed on Jul. 9, 2018.

(51) Int. Cl.
*C12M 1/00* (2006.01)
*C12N 1/12* (2006.01)
*C12M 1/34* (2006.01)

(52) U.S. Cl.
CPC ............ *C12M 29/14* (2013.01); *C12M 29/04* (2013.01); *C12M 41/12* (2013.01); *C12N 1/12* (2013.01)

(58) Field of Classification Search
CPC ...... C12M 29/14; C12M 41/12; C12M 29/04; C12M 21/02; C12N 1/12
See application file for complete search history.

(56) References Cited

U.S. PATENT DOCUMENTS

| 6,557,492 | B1* | 5/2003 | Robohm ............... A01K 63/02 119/203 |
| 8,476,067 | B2 | 7/2013 | Morgan |
| 9,206,388 | B1 | 12/2015 | Collins |
| 2009/0148927 | A1 | 6/2009 | Schroeder et al. |

OTHER PUBLICATIONS

NCMA. Pricing & Shipping Information, ncma.bigelow.org. 2014;1-6.*
Wynne et al. Transportation of Warmwater Fish: Equipment and Guidelines. SRAC. 2011;390:1-8.*
Emerson. Tank Protection & Control. Emerson. 2016;1-61.*
Bremer, Philip J. et al. Laboratory scale Clean-in-Place (CIP) studies on the effectiveness of different caustic and acid wash steps on the removal of dairy biofilms, *International Journal of Food Microbiology* 106 (2006) 254-262.
Geigert, John et al. Role of Quality Control in Validation of Biopharmaceutical Processes: Case Example of Clean-in-Place (CIP) Procedure for a Bioreactor, *PDA Journal of Pharmaceutical Science & Technology*, 48 (1994) 236-240.
Myers, Ted et al. Approaches to Cycle Development for Clean-in-Place Processes, *Journal of Parenteral Science & Technology*, 41 (1987) 9-15.
Palmowski et al. A Review of Current Technology and its Use in the Food and Beverage Industry, Deakin University, 2005, http://dmsc.com.au/dmsc/reports/Reports_Clean-in-Place-review_Deakin-University.pdf.
Roy, Kevin et al. Multivariate Statistical Monitoring as Applied to Clean-in-Place (CIP) and Steam-in-Place (SIP) Operations in Biopharmaceutical Manufacturing, *Biotechnol Prog*, 30 (2014) 505-515.

* cited by examiner

*Primary Examiner* — Lynn Y Fan
(74) *Attorney, Agent, or Firm* — Marianne Fuierer; Olive Law Group, PLLC

(57) ABSTRACT

The present invention provides for a method and transport system for conditioning micro algae grown in a commercial farm and transporting to a final destination while maintaining conditions that allow the microalgae to remain alive and healthy during transit.

7 Claims, 3 Drawing Sheets

SYSTEM AND METHOD FOR TRANSPORTING ALGAE

CROSS-REFERENCE TO RELATED APPLICATION

This application claims priority to U.S. Provisional Patent Application Ser. No. 62/695,262 filed on Jul. 9, 2018, the contents of which are incorporated by reference herein for all purposes.

BACKGROUND OF THE INVENTION

Technical Field

The present invention provides for a method and transport system for conditioning micro algae grown in a commercial farm and transporting to a final destination while maintaining conditions that allow the microalgae to remain alive and healthy during transit.

Related Art

Microalgae and cyanobacteria (for short, algae) are micro-plants and represent a very diverse group of organisms. They naturally produce many novel, as yet largely untapped classes of bioproducts. Globally, annual sales of algae-derived products (pharmaceuticals, nutraceuticals, agrochemicals, human food, and animal feed) has risen sharply in the last ten years. By taking advantage of the latest breakthroughs in molecular biology, metabolic engineering and functional genome research, algae can serve as an excellent gene-expression vehicle for production of recombinant proteins and other biologically active compounds for human and animal health and nutrition.

Further, due to the ability to rapidly uptake nutrients (such as carbon dioxide, nitrogen, and phosphorous) from the surrounding environment and converting them into organic compounds such as proteins stored in the cell, algae have been proposed and tested in natural and engineered systems to remove and recycle waste nutrients from wastewater and carbon dioxide-rich flue gases emitted from fossil fuel-fired power generators. The algal biomass produced as a by-product of the bioremediation process can then be used as feedstock for production of biofuels (such as biodiesel, ethanol, or methane), animal feed additives, and organic fertilizer.

Although applications of algae for renewable biofuels of both liquid and gaseous forms, high-value products and for environmental bioremediation is scientifically and environmentally sound, economic viability of algal applications is determined by the growth efficiency and ease of movement from one facility to another.

Presently the transportation of live microalgae is limited to very small quantities. These quantities are normally for seed stock or academic investigations for specific compounds or materials that may exist in the algal biomass. Often, these small quantities are shipped at cold temperatures, that being near 0° C. or below, which requires a heat sink and package insulation to prevent warming which will ultimately kill the microalgae. To avoid the negative effects of freezing and cell damage, if live microalgae is needed in large commercial quantities then the microalgae must be grown proximate to the final use point.

Thus, it would be advantageous to provide a system and method for transporting algae from one destination to another without implementing full growth conditions or adaptation for about a 0° C. environment while maintaining the viability of the transported algae.

SUMMARY OF THE INVENTION

The present invention provides for a method and system for preconditioning micro algae grown in a commercial farm and transporting to a final destination while maintaining conditions that allow the microalgae to remain alive and healthy during transit.

In one aspect the present invention provides for a system for transporting live algae from one algae growth facility to another algae growth facility, wherein the system comprises:

an insulated storage tank for holding liquid and live algae dispersed therein and wherein the insulated storage tank is adapted or adaptable for transport of the live algae at a temperature ranging from about 40 to about 50° F.; and an oxygen or sterilized air source communicatively connected to the insulated storage tank to provide a stream of replenishing oxygen or sterilized air to the liquid and live algae. The oxygen or sterilized air is preferably introduced into the tank at a flow of approximately 7 to 15 Standard Cubic Feet per Minute (scfm) and at a pressure of about 30 to about 140 psi using a small blower/compressor and sterilizing filter.

Notably, like all green plants, algae produce oxygen as a by-product of photosynthesis during the daylight hours or exposed to visible light frequencies. However, in darkness, such as in the storage tank of the present invention, algae consume oxygen, and as such, depending on the length of time in the transport tank, oxygen or sterilized air is preferably added.

In another aspect, the present invention provides for a method of transporting live algae in an insulated storage tank comprising a concentration of about 0.5 to 20 grams of live algae per liter of water in the insulated storage tank and more preferably from about 0.5 to 10 grams of live algae per liter of water, maintaining the live algae at a temperature ranging from about 40 to about 50° F., providing replenishment of oxygen or air to the insulated storage tank, thereby allowing transported algae to survive up to 2 weeks for long distance transport. In some systems, the live algae can be in a concentration of about 0.5 to 1 gram of live algae per liter of water.

The present system and method are applicable for all types of algae. Notably, there are approximately 100,000 known species of algae around the world and it is estimated that more than 400 new species are discovered each year. Algae are differentiated mainly by their cellular structure, composition of pigment, nature of the food reserve, and the presence, quantity, and structure of flagella. Algae phyla (divisions) include, for example, blue/green algae (Cyanophyta), euglenids (Euglenophyta), yellow/green and golden/brown algae (Chrysophyta), dinoflagellates and similar types (Pyrrophyta), red algae (Rhodophyta), green algae (Chlorophyta), and brown algae (Phaeophyta).

To improve the method of the present invention, it would be beneficial to the live algae to be preconditioned for the cooler temperatures before inclusion in the insulated storage tank. Such preconditioning may include a gradual cooling of the living conditions of the live algae while still providing nutrients to initiate the equivalence of suspended animation of the live algae. Such preconditioned algae will need little to no nutrients to survive over the time of transportation and photosynthesis will cease due to lack of sunlight or electromagnetic frequencies of visible light.

In another aspect the present invention provides for a method of transporting live algae to a destination requiring at least 1 day of travel and preferably for at least 2 days to 2 weeks of travel, the method comprising:

a) providing a transport system comprising.
  an insulated storage tank for holding liquid and live algae dispersed therein and wherein the insulated storage tank is adapted or adaptable for transport of the live algae at a temperature ranging from about 40 to about 50° F.; and
  an oxygen or sterilized air source communicatively connected to the insulated storage tank to provide a stream of replenishing oxygen or sterilized air to the liquid and live algae;
b) preconditioning the live algae for approximately 2 days to 5 days to adapt to temperatures ranging from about 40 to 50° F.;
c) introducing the live algae to the insulated storage tank in a density ranging from about 0.5 to 1 g per liter of water in the insulated storage tank;
d) maintaining levels of oxygen in the insulated storage tank in a sufficient amount to maintain viability of live algae; and
e) removing live algae from the insulated storage tank at the destination.

Various other aspects, features and embodiments of the invention will be more fully apparent from the ensuing disclosure and appended claims.

DETAILED DESCRIPTION OF THE PREFERRED EMBODIMENT

Figure 1:
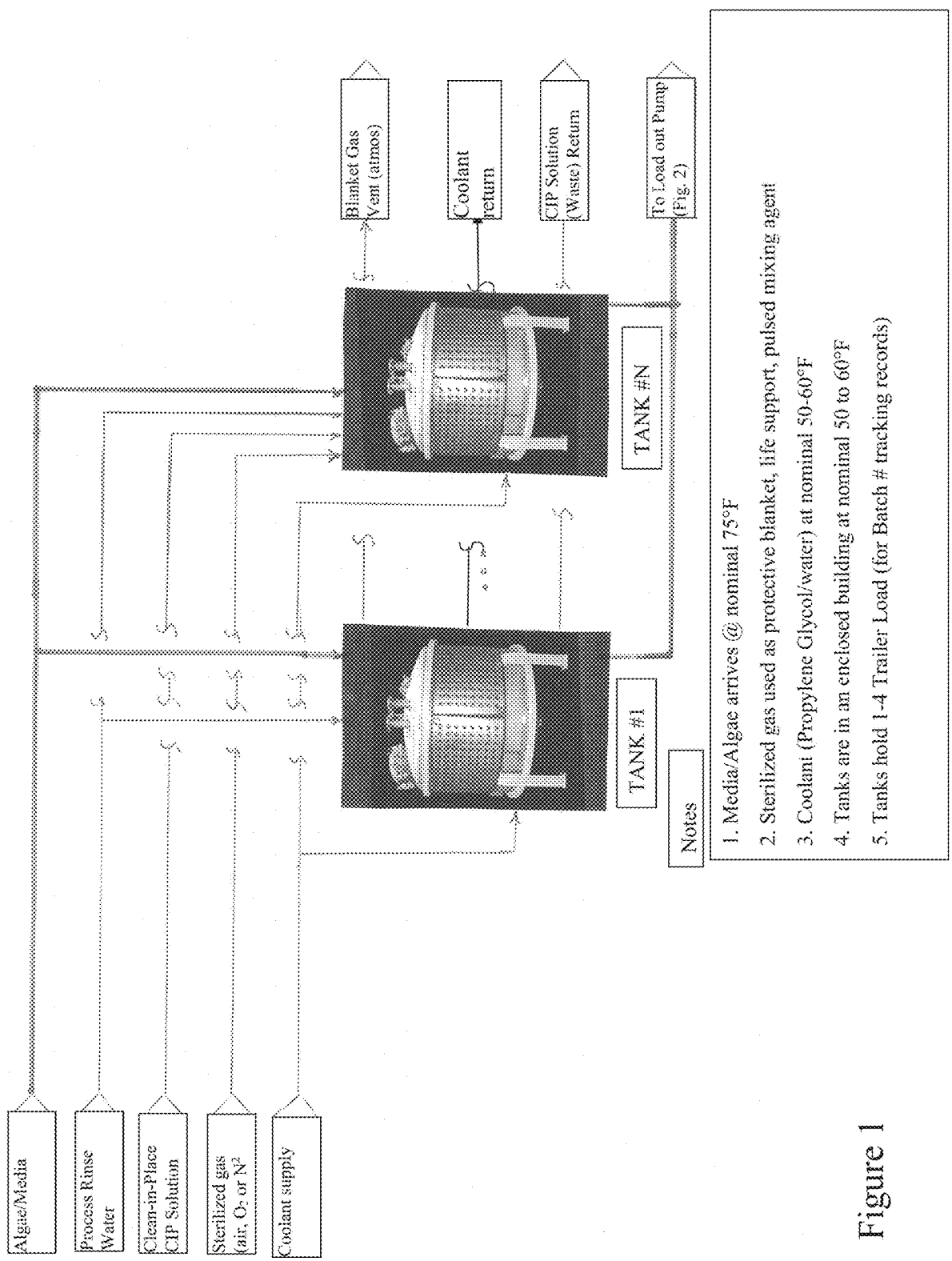
FIG. 1 is a perspective view of a micro algae storage facility which would be located at the micro algae growing farm. It provides the conditions needed for sustaining healthy micro algae existence and life. These conditions include the temperature and suitable utilities necessary to condition the micro algae for its journey to the final use point. Notably the tanks are sized to hold up to 4 trailers but in single compartments.
Figure 2:
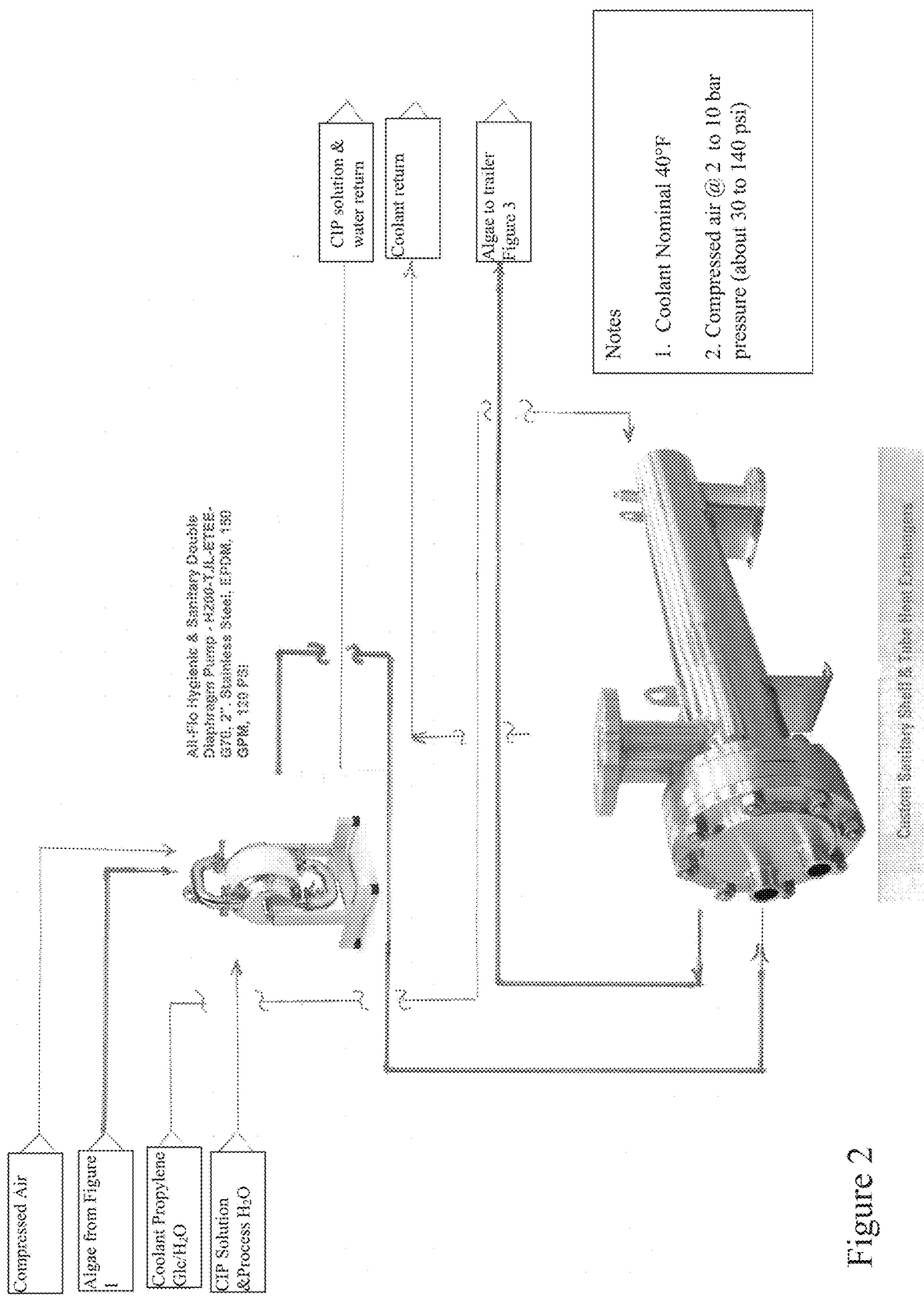
FIG. 2 is a schematic representation of the transfer system needed to move the micro algae (contained in a concentrated form in suitable life support media) to the vehicle which will accomplish the actual transportation to the final use point.
Figure 3:
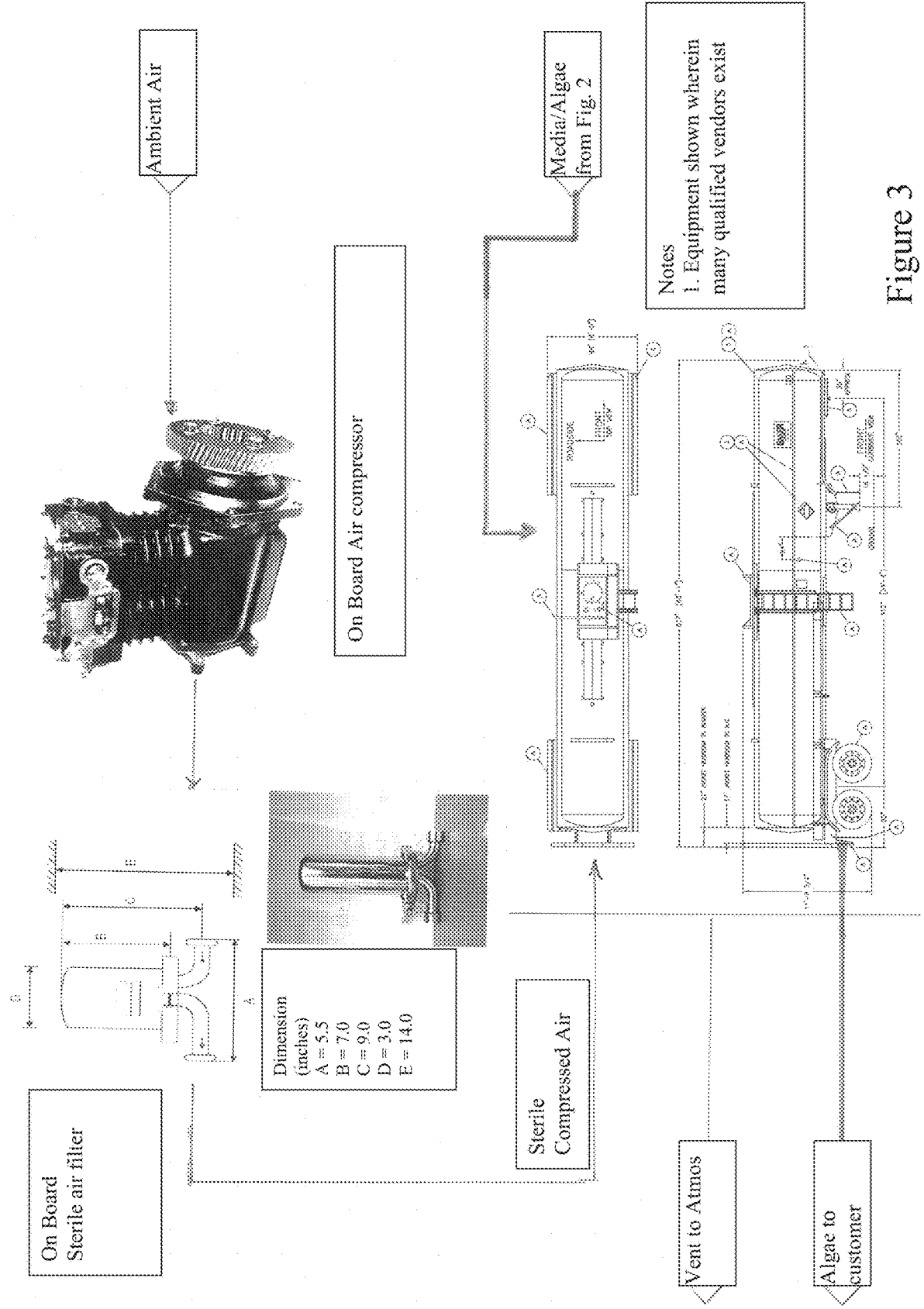
FIG. 3 is a representation of the portable storage tank and tractor which will deliver the concentrated micro algae to its final destination. These devices are widely available and currently used for delivery of such commodities as fresh orange juice, milk or other perishable items. The tanks are suitable insulated to allow very small temperature increases (typically less than 1 degree Celsius per day) from ambient heating. The required additional equipment required for micro algae transport is also shown.

Unless defined otherwise, all technical and scientific terms used herein have the same meaning as commonly understood by one of ordinary skill in the art to which this invention belongs. As used herein the following terms have the following meanings.

It must be noted that as used herein and in the appended claims, the singular forms "a", "an", and "the" include plural referents unless the context clearly dictates otherwise. Thus, for example, reference to "a compound" includes a plurality of compounds.

The term "about" when used before a numerical designation, e.g., temperature, time, amount, concentration, and such other, including a range, indicates approximations which may vary by (+) or (−) 10%, 5% or 1%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Basically, the system uses current equipment used to transport fresh orange juice and whole milk in bulk. These tankers are heavily insulated and only "gain" about 1-2 degrees F. per day during hot weather. Food grade tanker trucks are specifically designed to transport liquid food. The most common food item carried by tanker trucks is milk, but these trucks can carry the live algae to fill these tankers. Food grade tanker trailers, usually tube type tankers having a single tank or multiple ones for carrying different types of alive inactive algae. The tankers are required to meet stringent safety and sanitation codes before they are certified to transport foods and must be constructed of non-toxic and non-corrosive material. Preferably the interior of the storage tank is constructed of a non-porous and smooth material that resist binding or clinging of the algae to the interior surface. This allows for easy removal of the live algae when the destination is reached. Such interior coating can be stainless steel, polymeric, such as polyethylene, glass type coating, etc.

As stated above such trucks need to be insulated to maintain the optimal temperature to ensure the reduced activity of the live algae during the transport. In the alternative the insulated storage tank can be free standing but adaptable for movement by rail or air transport. Again, the storage tank must be insulated to maintain the temperature and has the ability to be communicatively connected to a source of replenishing oxygen or sterilized air.

The system may use available equipment used to transport liquid food products. Such food tankers are heavily insulated and only "gain" about 1-2 degrees F. per day during hot weather. If the algae and liquid, in a concentration of about 0.5 to 10 gram per liter, are cooled to 45 degrees F. before including in the tank, the algae can survive up from a few days to 2 weeks.

Preferably, the storage tanker is further equipped with a system for introducing oxygen or sterilized air into the storage tanker. As stated above, algae produce oxygen as a by-product of photosynthesis during the daylight hours or exposed to visible light frequencies. However, in darkness, such as in a dark storage tank of the present invention, algae consume oxygen, and as such, depending on the length of time and temperature in the transport tank, oxygen or sterilized air is preferably added.

Cool water generally holds more dissolved oxygen. However, once water temperatures drop below freezing and the water turns to ice, oxygen becomes unavailable to most organisms. Warm water holds only 7.4 mg/L of dissolved oxygen at 90-degrees (F), whereas 45-degree water can hold 11.9 mg/L. Notably, with a preferred temperature between about 40 and 50° F. in the movable storage tank, the addition of oxygen, alone or in sterilized air, should be in an about to maintain a level of oxygen from about of about 3 mg/L to about 11 mg/L of water.

Importantly, with the influx of oxygen or sterilized air with a sufficient content of oxygen, into the storage tank, there will be an increase of pressure therein. As such, a mechanism for release of increased pressure will be necessary. Venting through at least one positive check valve, or plumbing trap, is important for release of additional air molecules causing increased pressure in the storage tank. Preferably, the at least one positive check valve is adjusted to above atmospheric pressure, for release of pressure within tank thereby maintaining a sufficient amount of pressure in the storage tank to maintain the algae but also prevent outside air from entering into the storage tank. Positive pressure within the tank is important to prevent an unwanted debris or bodies from entering into the tank through the venting system. The positive pressure within the tank is preferably maintained above atmospheric pressure and more preferably at about the pressure on the outside of the tank, whether moving or in a stationary position. The positive pressure within the tank can be about 0.025 to 0.25 atm above that of the pressure on the outside of the tank.

A plumbing vent is also effective for relieving pressure within the storage tank. For example, a cyclone sewer plumbing vent uses the power of wind as the truck moves to draw the increased pressure out of the tank. The cyclone vent rotates 360 degrees and creates a vortex that pulls the pressure up and away from the storage tank.

Notably, algae (a plant) produces oxygen during the day with exposure to light or comparable electromagnetic radiation frequencies causing the process of photosynthesis due to the absorption of $CO_2$. However, in the present invention the algae are maintain in the dark and thus the reverse reaction is occurring. As such, plants actually reverse the process and produce carbon dioxide during lack of sunlight. In light of this reverse, an increase in $CO_2$ may be found in the tank and such an increase can cause a reduction in pH. An increase in acidity due to a changing pH can be addressed by adding a buffer to the tank to maintain a neutral pH and a healthy environment. Such buffering compound may include an ammonia gas or bicarbonate type compound.

Notably, even with an insulated storage tank, a difference in water temperature can create a layering effect throughout the water, with warmer water on top and cooler water below. This thermal stratification can limit the ability of oxygen to mix between the layers, resulting in different levels of oxygen in the tank with the possibility of decreased oxygen in some layers.

To ensure that oxygen level is sufficiently distributed through multiple water layers, the introduction of oxygen or oxygen containing air is preferably introduced under pressure and can be introduced in a pulsing fashion to ensure mixing of different layers within the tank. In the alternative the oxygen or oxygen containing air is introduced to a manifold system positioned at the bottom of the storage tank. With the introduction of the oxygen or oxygen containing air to the bottom of tank and through the manifold, there is subsequent bubbling through the layers of liquid to insure adequate mixing through the entire tank.

Preferably, there is at least one manifold for distributing the oxygen or oxygen containing air along the longitudinal axis of the tank. Multiple manifolds can be positioned parallel to each other. A manifold includes a multiplicity of opening or vents for distribution of the oxygen through the longitudinal axis of the tank to provide for a bubbling stream of $O_2$ the length of the tank. Such distribution provides for a mixing of the different layers in the tank thereby reducing cold and warm layers within the tank and equal distribution of oxygen in the tank.

Optionally, the storage tank can comprise a temperature control system, if needed, to maintain the temperature within the storage tank ranging from about 40 to about 50° F. Further the storage tank may further comprise baffles to control movement of the liquid within the tank during transport.

That which is claim is:

1. A method for transporting live algae to a destination requiring at least 1 day of travel, the method comprising:
    providing a transport system comprising;
        an insulated storage tank for holding an aqueous liquid and live algae dispersed therein, wherein the insulated storage tank is adapted or adaptable for transport of the live algae at a temperature ranging from about 40 to about 50° F. by including a temperature control system and wherein the insulated storage tank is devoid of access to visible light or electromagnetic radiation have frequencies of visible light thereby reducing or eliminating photosynthesis by the live algae; and
        an oxygen or sterilized air source communicatively connected to the insulated storage tank to provide a stream of replenishing oxygen or sterilized air to the aqueous liquid and live algae and wherein the oxygen or sterilized air is maintained under positive pressure within the insulated storage tank;
    preconditioning the live algae for approximately 2 days to 5 days to adapt to temperatures ranging from about 40 to about 50° F. while still providing nutrients to the live algae;
    introducing the live algae to the insulated storage tank in a density ranging from about 0.5 to 10 g per liter of water to maintain a concentrated form of the live algae in the insulated storage tank wherein the water includes a buffering agent to maintain a neutral pH to address increased amounts of $CO_2$;
    maintaining levels of oxygen in the insulated storage tank in a sufficient amount to maintain viability of live algae; and
    removing live algae from the insulated storage tank at the destination.

2. The method of claim 1, where the travel time is from 2 days to 2 weeks of travel.

3. The method of claim 1, wherein the flow for introducing oxygen or sterilized air is approximately 7 to 15 Standard Cubic Feet per Minute (scfm) at about 30 to 140 psi and using a small blower/compressor and sterilizing filter.

4. The method of claim 1, wherein the insulated storage tank further comprises additional components for adjusting conditions within the insulated storage tank selected from the group consisting of at least one manifold positioned at the bottom of the insulated storage tank, wherein the at least one manifold comprises a multiplicity of vents or openings for passage of oxygen or air containing oxygen into the insulated storage tank for bubbling a stream of $O_2$ into the insulated storage tank, at least one positive check valve position on an opening of the insulated storage tank for release of increased pressure within the insulated storage tank, and at least one baffle positioned within the insulated storage tank to control movement of the liquid therein during transport.

5. The method of claim 1, wherein the algae are selected from the group consisting of blue/green algae, euglenids, yellow/green and golden/brown algae, dinoflagellates and similar types, red algae, green algae, and brown algae.

6. The method of claim 4, wherein the positive pressure is maintained within the insulated storage tank to inhibit unwanted debris or bodies from entering into the insulated storage tank through a venting system.

7. The method of claim 6, wherein the positive pressure within the insulated storage tank is maintained above pressure on the outside of the insulated storage tank, whether moving or in a stationary position.

* * * * *